United States Patent
Bouazza et al.

(10) Patent No.: US 10,497,938 B2
(45) Date of Patent: Dec. 3, 2019

(54) BATTERY

(71) Applicant: Novaled GmbH, Dresden (DE)

(72) Inventors: Sofiane Bouazza, Leinfelden (DE); Carla Bobbio, Munich (DE); Ansgar Werner, Dresden (DE)

(73) Assignee: Novaled GmbH, Dresden (DE)

( * ) Notice: Subject to any disclaimer, the term of this patent is extended or adjusted under 35 U.S.C. 154(b) by 92 days.

(21) Appl. No.: 14/898,993

(22) PCT Filed: Jun. 5, 2014

(86) PCT No.: PCT/EP2014/061738
§ 371 (c)(1),
(2) Date: Dec. 16, 2015

(87) PCT Pub. No.: WO2014/202399
PCT Pub. Date: Dec. 24, 2014

(65) Prior Publication Data
US 2016/0141622 A1    May 19, 2016

(30) Foreign Application Priority Data

Jun. 21, 2013  (EP) .................................... 13173170
Jul. 30, 2013  (EP) .................................... 13178477

(51) Int. Cl.
*H01M 4/60* (2006.01)
*C07C 255/31* (2006.01)
*H01M 10/0525* (2010.01)

(52) U.S. Cl.
CPC ............ *H01M 4/60* (2013.01); *C07C 255/31* (2013.01); *H01M 10/0525* (2013.01); *H01M 2220/20* (2013.01); *H01M 2220/30* (2013.01)

(58) Field of Classification Search
None
See application file for complete search history.

(56) References Cited

U.S. PATENT DOCUMENTS 3,963,769 A  *  6/1976  Fukunaga ............... C07C 45/68
                                                              106/31.2
8,911,645 B2    12/2014  Hartmann et al.
(Continued)

FOREIGN PATENT DOCUMENTS

EP         1988587 A1  *  11/2008  ........... H01L 51/002
JP         S57-210567 A    12/1982
(Continued)

OTHER PUBLICATIONS

De Oliveira et al., "Bis(dicyanomethylene)squarate Squaraines in Their 1,2- and 1,3-forms:Synthesis, Crystal Structure and Spectroscopic Study of Compounds Containing Alkali Metals and Tetrabutylammonium Ions," Journal of Molecular Structure, 2009, 936:239-249. (Year: 2009).*

(Continued)

*Primary Examiner* — Daniel S Gatewood
(74) *Attorney, Agent, or Firm* — Eversheds Sutherland (US) LLP (57) ABSTRACT

The present invention relates to a battery that includes at least one electrochemical cell. The at least one electrochemical cell includes a first electrode, a second electrode, a first electroactive material, a second electroactive material, and an electrolyte which is in contact with both electrodes, and at least one of the first electroactive material and the second electroactive material includes a radialene compound. Also provided is an electroactive material as well as a radialene compound.

12 Claims, 4 Drawing Sheets

(56) References Cited

U.S. PATENT DOCUMENTS

| | | | |
|---|---|---|---|
| 2004/0115529 A1 | 6/2004 | Nakahara et al. | |
| 2012/0308890 A1* | 12/2012 | Okuda | H01M 4/131 |
| | | | 429/218.2 |

FOREIGN PATENT DOCUMENTS

| | | | |
|---|---|---|---|
| JP | 2009-196925 A | | 9/2009 |
| JP | 2009196925 A | * | 9/2009 |
| JP | 2011-165567 A | | 8/2011 |
| JP | 2011165567 A | * | 8/2011 |
| JP | 2013-020741 A | | 1/2013 |

OTHER PUBLICATIONS

Farnia, et al., "Dicyanomethylene derivatives of squaric acid: electrochemical behaviour and ESR investigation", J Electroanal Chem., 404, 261-269, 1996 (Year: 1996).*

PCT International Search Report for PCT Application No. PCT/EP2014/061738 dated Jul. 29, 2014 (4 pages).

Cortadellas et al., "Nickel Coordination Compounds of the Cyanamide Squarate Ligand. The Crystal Structures of the 2,4-bis(cyanamido)cyclobutane-1,3-dione dianion (2,4-NCNsq2-) and of Three Polymers with General Formula [Ni(Him)x(H2O)4-x(2,4-NCNsq) · tG2l]n (x=2-4; y=1-3; Him=imidazole)," Inorganica Chimica Acta, 2006, 359:484-496.

Despotovic et al., "The Structure and Stability of [3]-Radialenes and Their Danions—A DFT Study," Journal of Molecular Structure:Theochem, 2007, 811:313-322.

De Oliveira et al., "Bis(dicyanomethylene)squarate Squaraines in Their 1,2- and 1,3-forms:Synthesis, Crystal Structure and Spectroscopic Study of Compounds Containing Alkali Metals and Tetrabutylammonium Ions," Journal of Molecular Structure, 2009, 936:239-249.

Fukunaga, "Negatively Substituted Trimethylenecyclopropane Dianions," J. Am. Chem., Soc., 1976, 98(2):610-611.

Fukunaga, "Negatively Substituted Trimethylenecyclopropane and Their Radical Anions," J. Am. Chem., Soc., 1976, 98(2):612-613.

Koch et al., "New Anions as Supporting Electrolytes for Rechargeable Lithium Batteries," Journal of Power Sources, 1987, 20:287-291.

* cited by examiner

BATTERY

CROSS REFERENCE TO RELATED APPLICATIONS

This application is a U.S. national stage application of PCT/EP2014/061738, filed Jun. 5, 2014, which claims priority to European Application Nos. 13173170.5 and 13178477.9 filed Jun. 21, 2013 and Jul. 30, 2013, respectively. The contents of these applications are hereby incorporated by reference.

TECHNICAL FIELD

The present invention relates to a battery comprising at least one electrochemical cell comprising a first electrode, a second electrode, a first electroactive material, a second electroactive material and an electrolyte which is in contact with both electrodes. The present invention also relates to electroactive materials as such and compounds suitable therefore.

BACKGROUND OF THE INVENTION

Batteries comprising electrochemical cells serve widespread as mobile low-voltage direct current electricity sources. Present-day most frequently used secondary (rechargeable) batteries are lithium ion batteries. Such kind of battery can be built e.g. using transition metal oxide that contains lithium cations in the first electrode and crystalline or amorphous carbon in the second electrode as active materials, with a lithium salt as an electrolyte. The charging is then performed via connecting the first electrode to the positive pole of an external voltage source and the second electrode to the negative pole of the external voltage source, what results in an oxidation of the transition metal in the first electrode polarized as anode, deintercalation of the Li cations from the anode, their electromigration through the electrolyte, their reduction on the second electrode polarized as cathode, and in the intercalation of the formed electrically neutral Li atoms in the carbon matrix of the second electrode. When discharging this battery by connecting its poles to an external electrical resistance, the first electrode as the positive pole of the battery consumes electrons coming through the external circuit from the second electrode that represents the negative pole of the battery. The first electrode in the discharging battery is called cathode, because there takes place an electrochemical reduction of the transition metal to its lower valence, accompanied by intercalation of the Li cations form the electrolyte. The second electrode in the discharging battery is assigned, according to the electrochemical convention, as anode, because there takes place an electrochemical oxidation of the intercalated Li atoms, releasing electrons in the external circuit and Li cations in the electrolyte.

In batteries for the most of consumer devices, energy storage and operating time are the keys, so the more the better. Especially for mobile applications like cell phones, electric vehicles (EV) or hybrid vehicles (HEV), higher power and energy densities are required.

In this regard, electrochemically active materials play an essential role. For the use in rechargeable batteries, only highly reversible redox systems are applicable. For allowing high energy density, low molecular weight compounds exchanging high number of electrons per molecule or polymers with low molecular weight building units exchanging high number of electrons per building units are preferable, most preferably those showing, moreover, high redox potential. Among further (often somewhat contradictory) requirements on electroactive materials for batteries can be named their safety, intrinsic chemical stability and low aggressiveness, good mechanical properties, easy processability, environmental tolerability, abundance of necessary raw materials and low manufacturing cost. Solid or gel-like electroactive materials are preferred.

As an alternative to transition metal based inorganic redox-active materials, electroactive organic materials offer potential advantages in their light weight, low-temperature processability, raw material accessibility and lowering the environmental burden by absence of toxic metals like nickel. Examples of organic electroactive materials recommended for use in batteries are nitroxide compounds reported e.g. in US2004/115529 or tetracyanoquinodimethane (TCNQ) reported in Japanese patent application S57-210567. Yet, the performance of organic electroactive materials, especially in terms of their electrical properties, energy density, reversibility and stability, has to be significantly improved.

The object of the present invention is to provide batteries with improved energy density. Another object of the invention is to provide electroactive organic materials with improved energy density and sufficient stability and reversibility for their use in rechargeable batteries. Yet another object of the invention is to provide new compounds enabling the inventive electroactive organic material and batteries comprising it.

SUMMARY OF THE INVENTION

The object of the invention is achieved by battery comprising at least one electrochemical cell comprising a first electrode, a second electrode, a first electroactive material, a second electroactive material and an electrolyte which is in contact with both electrodes, wherein at least one of the first electroactive material and the second electroactive material comprises a radialene compound.

Preferably, the electroactive material comprising a radialene compound is the first electroactive material comprised in a first compartment of the electrochemical cell comprising the first electrode, and the first electrode is electrically connected with positive pole of the battery. In this embodiment, a reduction of an electroactive radialene compound runs on the first electrode, if the cell is operating in the discharging mode.

Also preferably, the radialene compound is selected from radialene compounds having their carbocyclic core substituted with groups independently selected from oxo, imino and methylidene, wherein the imino and methylidene groups are substituted with electron withdrawing substituents.

More preferably, the radialene compound is selected from [3]radialene and [4]radialene compounds having their cyclopropane or cyclobutane core substituted with groups independently selected from oxo, imino and methylidene, wherein the imino and methylidene groups are substituted with electron withdrawing substituents. Even more preferably, the electron withdrawing substituents are cyano groups.

Also preferably, the radialene compound has the general formula (I)

wherein $Z^1$, $Z^2$ and $Z^3$ are independently selected from dicyanomethylidene, oxo and cyanimino group, x is an integer selected from 1 and 2, y is an integer selected from 0, 1 and 2 and the dashed lines represent
i) for y=0,
6 electrons delocalized over 6 bonds if x=1 and
8 electrons delocalized over 8 bonds if x=2,
ii) for y=1,
7 electrons delocalized over 6 bonds if x=1 and
9 electrons delocalized over 8 bonds if x=2,
iii) for y=2,
8 electrons delocalized over 6 bonds if x=1 and
10 electrons delocalized over 8 bonds if x=2.

More preferably, at least one group selected from $Z^1$ and $Z^2$ and at least one group $Z^3$ is dicyanomethylidene. Also preferably, one or two groups independently selected from $Z^1$, $Z^2$ and $Z^3$ are oxo groups.

Preferably, the electrolyte comprises alkali metal cations. Also preferably, the first electroactive material in its reduced state comprises alkali metal cations. Also preferably, the second electroactive material in its reduced state comprises an alkali metal. More preferably the alkali metal cation is $Li^+$. Most preferably, the alkali metal is Li.

Another object of the invention is achieved by the electroactive material comprising a radialene compound.

Preferably, the electroactive material comprising a radialene compound is solid or gel-like.

More preferably, the radialene compound is selected from radialene compounds having their cycloalkane core substituted with groups independently selected from oxo, imino and methylidene, wherein the imino and methylidene groups are substituted with electron withdrawing substituents.

Also preferably, the radialene compound is selected from [3]radialene and [4]radialene compounds having their cyclopropane or cyclobutane core substituted with groups independently selected from oxo, imino and methylidene, wherein the imino and methylidene groups are substituted with electron withdrawing substituents. Even more preferably, the electron withdrawing substituents are cyano groups.

Even more preferably, at least one electroactive compound has the general formula (I)

wherein $Z^1$, $Z^2$ and $Z^3$ are independently selected from oxo, imino and methylidene, the imino and methylidene groups are substituted with electron withdrawing substituents, x is an integer selected from 1 and 2, y is an integer selected from 0, 1 and 2 and the dashed lines represent
i) for y=0,
6 electrons delocalized over 6 bonds if x=1 and
8 electrons delocalized over 8 bonds if x=2,
ii) for y=1,
7 electrons delocalized over 6 bonds if x=1 and
electrons delocalized over 8 bonds if x 2,
iii) for y=2,
8 electrons delocalized over 6 bonds if x=1 and
electrons delocalized over 8 bonds if x=2.

Preferably, electron withdrawing groups are cyano groups. More preferably, at least one group selected from $Z^1$ and $Z^2$ and at least one group $Z^3$ is dicyanomethylidene. Also preferably, one or two groups independently selected from $Z^1$, $Z^2$ and $Z^3$ are oxo groups.

Also preferably, the electroactive material in its reduced state comprises alkali metal cations.

More preferably, the alkali metal cations are lithium cations.

Yet another object of the invention is achieved by the compound having formula (II), wherein $Z^1$, $Z^2$ and $Z^3$ are independently selected from dicyanomethylidene, oxo and cyanimino group, x is an integer selected from 1 and 2 and the dashed lines represent.
8 electrons delocalized over 6 bonds if x=1 and
10 electrons delocalized over 8 bonds if x 2.

Preferably, at least one group selected from $Z^1$ and $Z^2$ and at least one group $Z^3$ is dicyanomethylidene. Also preferably, one or two groups independently selected from $Z^1$, $Z^2$ and $Z^3$ are oxo groups.

Examples of preferred compounds are

DETAILED DESCRIPTION OF THE INVENTION

Radialene compounds within this application are the compounds having a carbocyclic core in the shape of a convex regular polygon, wherein each core carbon atom is attached by sigma bonds to two of its neighbour core carbon atoms and to just one substituent placed outside the core and having its bond to the corner of the polygon in the radial direction from the centre of the polygon. To comply with the formal carbon valence which is equal four, the substituents are formally attached to the corners of the carbocyclic core by double bonds. Of course, pielectrons in compounds formally described by means of alternating double and single bonds are more or less delocalized and a more accurate description of the bonding in them is possible e.g. in terms of resonance structures or molecular orbitals. The delocalization of pielectrons in radialene compounds provides these compounds with specific properties.

Fukunaga (J. Am. Chem. Soc. 1976, 98 (2), 610-611 and U.S. Pat. No. 3,963,769) and Fukunaga et al (J. Am. Chem. Soc. 1976, 98 (2), 612-613) described tris(methylene) cyclopropanes substituted with electron withdrawing groups as oxidants wherein the stronger electron withdrawing substituents are present, the more positive are the measured redox potentials. Such compounds could be potentially useful as electroactive component in electroactive materials for batteries.

Electroactive material is within this application defined as a condensed phase (solid or liquid) system comprising at least one electroactive component. Electroactive component is a compound which is able to create in an appropriately designed electrochemical cell a measurable voltage. In other words, all known oxidizing and/or reducing agents can be contemplated as potential electroactive compounds, however, compounds able to form reversible redox systems are strictly preferred. In rechargeable batteries, the best possible reversibility of electrochemical processes which take place in the used electroactive materials during battery charging and discharging is one of most important requirements for an industrially applicable electroactive material.

Unfortunately, all compounds reported by Fukunaga were not only very reactive, but also, with a sole exception of tris(diacetylmethylidene)cyclopropane which is a rather weak oxidant, intrinsically unstable. Especially, the most powerful oxidant tris(dicyanomethylidene)cyclopropane is a basically intractable compound that spontaneously decomposes under heating, reacts with common solvents and changes its colour quickly if stored in its solid state. Fukunaga reports its redox potential as high as +1.13 V vs saturated calomel electrode (SCE) as reference what corresponds to a value about +0.74 V vs ferrocenium/ferrocene ($Fc^+/Fc$) reference, nevertheless, he also reports that the measured cyclic voltammetry (CV) waves were not totally reversible.

Recently, the authors of the present application have confirmed that tris(dicyanomethylidene)cyclopropane is a very reactive and in its pure state synthetically difficult accessible strong oxidant. Nevertheless, they have surprisingly found that if the corresponding dianion occurs as an alkali metal salt in a solid or gel-like electroactive material that was placed in a cathode compartment of an electrochemical cell, the oxidized form created during the charging of the cell is more stable than a chemically prepared isolated compound, shows reversible redox electrochemical behavior and can be thus utilized as an electroactive component in rechargeable batteries. The same applies for various derivatives of general formula (I). It has been proven that through utilizing the inventive electroactive material in its electrochemically fully reduced state, the inventive electrochemical cell comprising compound (I) in the first electrode and/or in the first compartment adjacent to the first electrode can be safely built in its discharged state.

In electrochemical cells comprised in batteries, it is a widely used convention, to assign
- as a cathode the first electrode, wherein the spontaneous electrochemical reduction takes place during the discharging step, despite it is connected to the electrically positive electrical pole of the battery, and
- as an anode the second electrode, wherein the spontaneous electrochemical oxidation takes place during the discharging step, despite it is electrically connected to the electrically negative pole of the battery.

Thus, an appropriate first (cathode) electroactive material in the form prevailing in the charged cell shall be a strong oxidant, whereas in the reduced form prevailing in the discharged cell, it is a very weak reducing agent. Oppositely, an appropriate second (anode) electroactive material shall be in its reduced form prevailing in the charged cell a strong reducing agent, whereas in the oxidized form prevailing in the discharged cell, its oxidation ability is extremely weak.

The preferred inventive electroactive material perfectly fits with these requirements. In its fully reduced state, it comprises the compound (I) solely as a doubly charged anion having general formula (Ia), whereas in its electrochemically fully oxidized state, it comprises compound of the formula I solely in the electrically neutral form represented by general formula (Ib):

wherein $Z^1$, $Z^2$ and $Z^3$ are independently selected from oxo, imino and methylidene, the imino and methylidene groups are substituted with electron withdrawing substituents, x is an integer selected from 1 and 2, and the dashed lines represent i) for x 1,
  in compound (Ia) 8-electrons delocalized over 6 bonds, whereas in compound (Ib) only 6 electrons delocalized over 6 bonds, ii) for x=2,
  in compound (Ia) 10 electrons delocalized over 8 bonds, whereas in compound (Ib) only 8 electrons delocalized over 8 bonds.

Electron withdrawing substituents are generally the substituents that posses positive value of sigma constant in the Hammet equation as taught in physical organic chemistry textbooks.

Preferred are the substituents having the highest sigma values and the lowest relative molecular weights. Most preferred electron withdrawing group is the cyano group, therefore, the most preferred substituted imino and methylene groups are the cyanimino and dicyanomethylene groups.

Reduced form (Ia) is stable in form of salt with an appropriate cation. Preferred are salts with two alkali metal cations, more preferred are dilithium salts, even more preferred are the salts comprising two dicyanomethylene groups, as exemplified in formula (1a) or formulas (2a), (2a'):

The oxidized electrically neutral form (Ib) can be for x=1 shown in one of its mesomeric forms represented by formula (1b), for x=2, in one of its mesomeric forms represented by formulas (2b) and (2c).

The voltammograms shown in the experimental part below bring an evidence that compound (I) with a single negative charge (y=1) occurs as an intermediate form in the electrochemical reaction between the fully oxidized form (Ib) and fully reduced form (Ia). Nevertheless, it is supposed that it establishes the chemical equilibrium with both much more stable forms (Ia) and (Ib) with a rate high enough that it allows omitting the single-charged form from further consideration. The electrochemical potential of the inventive electroactive material according to the invention in any state between the fully oxidized state (Ib) and fully reduced state (Ia) is therefore given by the electrochemical equilibria of forms (Ia) and (Ib) in presence of other components of the inventive electroactive material.

Preferably, electroactive material comprising compound of formula (Ia) and/or (Ib) is comprised in the first electrode (cathode). Alternatively or additionally, the electroactive material comprising compound of formula (Ia) and/or (Ib)

may be comprised in the first (cathode) compartment of the electrochemical cell that is adjacent to the first electrode. It is preferred that the first compartment comprising compound of formula (Ia) and/or (Ib) is separated by a separator from the second compartment that is adjacent to the second electrode.

The inventive electroactive material may comprise electrochemically inactive components which do not change their redox state during operation of the inventive electrochemical cell. If the inventive electroactive material forms the first electrode, the electrochemically inactive components may be e.g. binders improving its mechanical properties or fillers improving its electrical properties. Typically, electrically conductive carbon black can be utilized as a filler improving conductivity, various polymers like polyethylene oxide, polyvinyl alcohol, polyacrylates, polyvinylidene fluoride, polyacrylonitrile and polysiloxanes may serve as binders.

The electroactive material according to the invention may be also mixed with another electroactive material to prepare a composite first electrode.

Alternatively or in addition, the first electrode may comprise a metal, a semiconductor or another solid with good conductivity for electrons, which does not react with compound of formula (Ia) and/or (Ib) nor with other compounds comprised in the compartment adjacent to the first electrode. Preferably, the metal or the solid with metallic conductivity forms a continuous layer having direct electrical contact with the pole of the battery which belongs to the first electrode. Also preferably, the continuous layer with metallic conductivity consists of a conductive oxide, of carbon or of a chemically inert metal like platinum, gold or silver, or of a chemically inert metal alloy. In the combination with such inert electrode and with an appropriate separator, the compound (I) may also occur in the whole first compartment of the inventive electrochemical cell, partially or fully dissolved in the electrolyte, which in this case can be considered also as an electrochemically inactive component of the inventive electroactive material.

The electrolyte used in the battery cells of the present invention may be an electrolyte solution prepared by dissolving an electrolyte salt in an appropriate solvent. The example of particularly preferred solvent may be a room temperature ionic liquid (RTIL). Alternatively or in addition, low molecular non-ionic solvents may be used. Preferred are polar aprotic solvents like diethyl carbonate or ethylene carbonate. Polymers like polyethylene oxide or polyvinyl pyrrolidone may be comprised in the electrolyte as a solvent or a component of the solvent too.

As RTIL, preferred are imidazolium, pyrrolidinium, and aliphatic quaternary ammonium type ionic liquids comprising cations like 1-ethyl-3-methyl-imidazolium, 1-butyl-3-methyl-imidazolium, 1-butyl-2-methyl pyrrolidinium, N-methyl-N-propylpiperidinium, N,N-diethyl-N-methyl-N-(2-methoxyethyl) ammonium. The anionic component contained in the ionic liquid may be $(CF_3SO_2)_2N^-$, $(C_2F_6SO_2)_2N^-$, $CF_3SO_3^-$, $C(CF_3SO_2)_3^-$, $PF_6^-$, $BF_4^+$, and $ClO_4^-$. These ionic liquids may be used alone or in combination with one or more other ionic liquids.

The electrolyte salt comprises the same cation that is chosen as the counter cation for the compound (Ia). Preferably, it is an alkali metal cation, more preferably, it is the lithium cation. Example of commercially available electrolyte salts comprising lithium cation are $LiN(CF_3SO_2)_2$, $LiN(C_2F_5SO_2)_2$, $LiCF_3SO_3$, $LiC(CF_3SO_2)_3$, $LiPF_6$, $LiBF_4$, and $LiClO_4$.

Alternatively (instead of the mentioned low molecular electrolyte salt) or in addition, solid polymeric electrolyte having the anionic groups covalently attached to the polymeric backbone may be used. It is preferred that the polymer used as the (co)solvent and/or as the electrolyte salt is crosslinked to form an infinite polymeric network.

A crosslinked and/or insoluble polymeric electrolyte may be used also as the separator dividing the electrochemical cell to two compartments—the first compartment adjacent to the first electrode and the second compartment adjacent to the second electrode. As a separator, an inert solid carrier like glass wool soaked with an appropriate liquid electrolyte like RTIL may be used as well.

The second electrode may be made of any commercially available materials currently supplied for use as anodes in discharging metal-ion batteries. Example of active materials for the second electrode include metal lithium, carbon materials, metal silicon, metal tin, metal aluminum, alloys of metals or semimetals like aluminum, lead, tin, silicon and magnesium with lithium, metal oxides like $SnO_2$, $TiO_2$, and conducting polymers like polyacetylene.

For better illustration of one of the preferred embodiments of the invention, the operation of a Li-ion rechargeable battery which comprises the electroactive compound of the formula (Ia) and/or (Ib) as an electroactive material in the first electrode and/or in the first compartment is explained below in detail.

During the charging of the inventive battery, the positive pole of the external voltage source is connected to the first electrode comprising a salt of formula (H). The salt is oxidized by supplying two electrons to the external circuit and releases its Li$^+$ countercations into the surrounding electrolyte, affording the corresponding electrically neutral molecule (Ib). Alternatively, the salt (Ia) in the charged cell is dissolved in the first compartment, and when releasing two electrons through the chemically inert first electrode into the external circuit, it leaves the corresponding electrically neutral molecule (Ib) in the first compartment, either dissolved or precipitating as a solid. The released lithium cations migrate in both cases to the second electrode.

On the second electrode connected to the negative pole of the external voltage source, the cations from the electrolyte or cations incorporated in the body of the second electrode attach the electrons supplied from the external circuit and form an electrically neutral form of the second electroactive compound.

Oppositely, during discharging, the oxidized form (Ib) is reduced to corresponding dianion (Ia) that forms with two lithium cations the salt (II). The mechanism of the reversible energy storage in the inventive electrochemical cell is depicted in the Scheme 1.

Scheme 1

BRIEF DESCRIPTION OF THE DRAWINGS

FIG. 1 shows a cyclic voltammogram of 2,2',2"-(cyclopropane-1,2,3-triylidene)trimalononitrile dilithium salt (1)

in an electrolyte consisting of 0.1M $LiPF_6$ in the mixture ethylene carbonate (EC):diethyl carbonate (DEC) having volume ratio v/v=1/2

FIG. 2 shows first charge/discharge curve vs. lithium at different charging rates of 2,2',2"-(cyclopropane-1,2,3-triylidene)trimalononitrile bis lithium salt (1) as cathode, lithium metal as anode, and 1M $LiN(CF_3SO_2)$ in 1-ethyl-3-methylimidazolium bis(trifluoromethylsulfonyl)imide as electrolyte.

FIGS. 5A, 5B, show the first charge/discharge curve vs. lithium at different charging rates of an electrochemical cell having 2,2'-(2,4-dioxocyclobutane-1,3-diylidene)dimalononitrile bis lithium salt (2) as cathode, lithium metal as anode, and 1M $LiN(CF_3SO_2)$ in 1-ethyl-3-methylimidazolium bis(trifluoromethylsulfonyl)imide as electrolyte. FIG. 5A shows charge/discharge at C/10 (8.2 mA/g). FIG. 5B shows charge/discharge at C/2 (35 mA/g).

EXAMPLES

Example 1

Dilithium salt of (3-(dicyanomethylene)cycloprop-1-ene-1,2-diyl)¬ bis¬ (dicyanomethanide) (1)

Step 1, Tetrabutylammonium (TBA) salt of (3-(dicyanomethylene)cycloprop-1-ene-1,2-diyl)bis¬ (dicyanomethanide) (Preparation is described in U.S. Pat. No. 3,963,769)

Under argon, sodium hydride (5.6 g, approx. 60 wt. % suspension in mineral oil, 7.0 eq) was washed with 3×30 mL hexanes, suspended in 130 mL anhydrous glyme and then cooled down to 4° C. with an ice/water bath. In 15 min, redistilled malononitrile (4.22 g, 3.2 eq.) in 15 mL anhydrous glyme was added dropwise (gas evolution). The beige slurry was stirred 1 h at 0° C., before tetrachlorocyclopropene (2.45 mL, 1.0 eq) in anhydrous glyme (7.0 mL) is added slowly (during ca. 15 min, gas evolution) to the reaction mixture. The brown slurry was stirred 1 h at 0° C., then let warm up slowly to the room temperature (rt). Dropwise addition of 5 mL distilled water to quench and then diluting the reaction mixture with 70 mL distilled water was followed by addition of aqueous tetrabutylammonium bromide (TBABr, 14.1 g, 2.2 eq. previously dissolved in 15 mL distilled water). The resulting slurry was stirred for 2 h and the formed precipitate was filtered. After thoroughly washing with water (5×30 mL), the brown precipitate was dried in vacuo or at air overnight. The solid was then dissolved in 200 mL acetonitrile (AN) and re-precipitated by addition 600 mL ethyl acetate (EA). Precipitation can be repeated once more to get a colorless solid.

Yield: 12.1 g (85%)
Analytics:
ESI-MS (in 100% AN) neg: 470, 228.
IR (solid, measured in the attenuated total reflectance (ATR) arrangement): 2962 m, 2936 m, 2865 m, 2182 s, 2163 s, 1412 s $cm^{-1}$.

Step 2, Lithium salt of (3-(dicyanomethylene)cycloprop-1-ene-1,2-diyl)bis¬ (dicyanomethanide), $Li_2C_{12}N_6$ (1):

Tetrabutylammonium (3-(dicyanomethylene)cycloprop-1-ene-1,2-diyl)bis(dicyano methanide) (12.0 g, 17.0 mmol) was dissolved in 230 mL AN, a solution 11.4 g lithium iodide (5.0 eq.) in 50 mL AN was added and the reaction mixture was heated at 80° C. under inert atmosphere for 20 h. The reaction mixture was cooled down to approx. 50° C. and the pale yellow precipitate was filtered under inert atmosphere. Washing with 3×15 mL AN and drying in vacuo afforded 2.65 g (64%) pale yellow solid.

Analytics:
ESI-MS (in 100% AN) neg: 228, 114 m/z.
IR (solid, ATR): 2223 s, 2195 s, 2170 s, 1638 m, 1425 s $cm^{-1}$.

Example 2

Lithium Salt of 2,2'-(2,4-dioxo-1,3-cyclobutanediyl) bis-propanedinitrile (2) Step 1, Sodium Salt of 2,2'-(2,4-dioxo-1,3-cyclobutanediyl)bis-propanedinitrile 0.94 g Sodium was dissolved in 100 mL dry ethanol and stirred over night. 3.1 g starting betaine 1,3-bis(dimethylamino)-2,4-dihydroxy-cyclo¬ butane¬ diylium (18.5 mmol) was added and the mixture stirred for 15 min, followed by addition of 2.44 g malonitrile. The mixture was refluxed for 3.5 h. After cooling to rt, the solid was filtered off and washed with ethanol. Drying was done in vacuum at 50° C./10 mbar over night.

Yield: 4.9 g (79%)
Analytics:
ESI-MS (in 100% AN) neg: 207.

Step 2, Tetrabutyl ammonium salt of 2,2'-(2,4-dioxo-1,3-cyclobutanediyl)bis-propanedinitrile The sodium salt of 2,2'-(2,4-dioxo-1,3-cyclobutanediyl) bis-propanedinitrile (2.9 g) was suspended in 60 mL water and 7.3 g TBABr dissolved in 60 mL chloroform were added at rt and stirred for 2 h. The mixture was poured into a separator funnel and three phases were obtained. The solid was filtered off, washed with small portions water and chloroform, and dried on a clay plate, then in vacuum at 50° C./10 mbar over night to give 3.9 g yellow powder. A cca 1.4 second crop of the product was obtained after stirring the filtrate for 1 week, filtration, washing with small portions chloroform and drying in vacuum at 50° C./10 mbar over night.

Yield: 3.9 g (50%, the first crop only)
Analytics:
ESI-MS (in 100% AN) neg: 208, 450.
IR (solid, ATR): 2961 m, 2874 m, 2176 s, 2155 s, 1580 s, 1369 $cm^{-1}$.

Step 3, Lithium Salt of 2,2'-(2,4-dioxo-1,3-cyclobutanediyl)bis-propanedinitrile (2)

In a glove box, TBA salt of 2,2'-(2,4-dioxo-1,3-cyclobutanediyl)bis-propanedinitrile (0.333 g/0.48 mmol) and LiI (0.300 g/2.24 mmol) were placed in a flask and 7.5 mL acetonitrile were added. A yellow precipitate occurred immediately. The mixture was allowed to stir over night. The precipitate was filtered off, washed with AN and dried in vacuum at 50° C./10 mbar over night to give 0.12 g (82%) yellow solid.

Analytics:

ESI-MS (100% AN) neg: 208.

IR (solid): 2196 s, 1594 m, 1543 s, 1383 s, 1364 s cm$^{-1}$.

Example 3

CV Measurement

Figure 1:
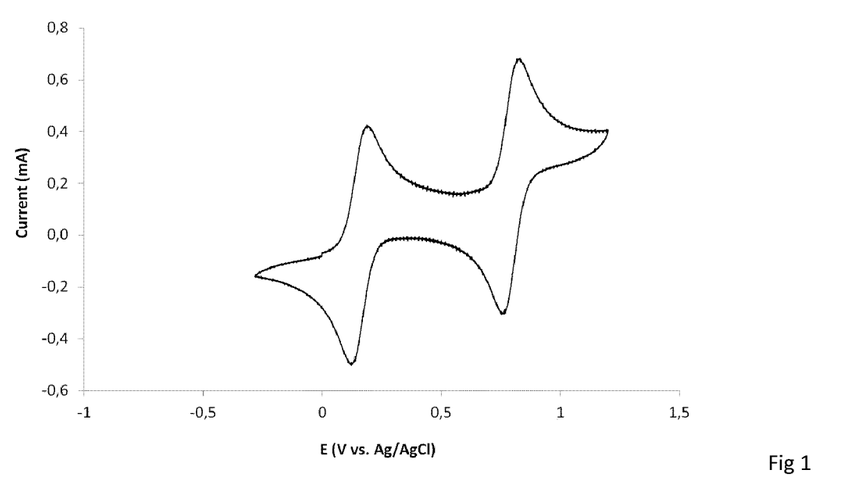
Figure 4:
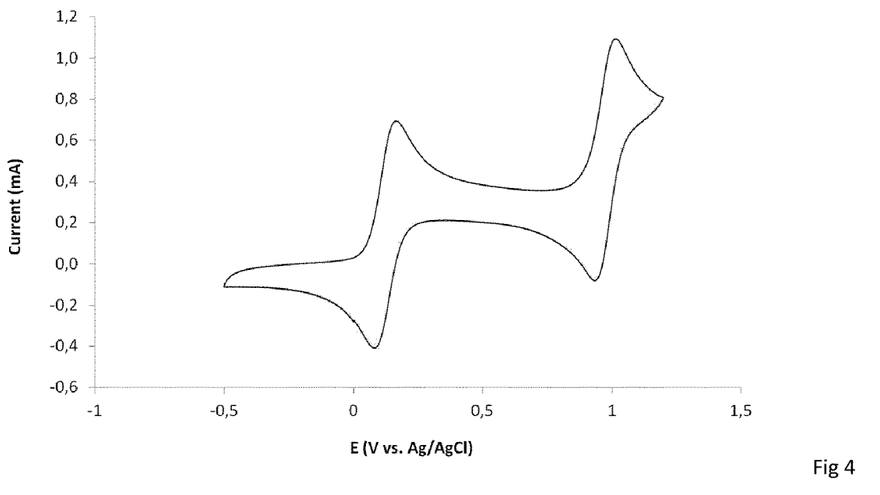
FIG. 4 shows a cyclic voltammogram of 2,2'-(2,4-dioxocyclobutane-1,3-diylidene)dimalononitrile bis lithium salt (2) in an electrolyte consisting of mixed solvent EC:DEC (v/v=1/2) with 0.1M $LiPF_6$ at scan rate of 50 mV/s at room temperature.

Cyclic voltammetry (CV) was performed using a three electrode glass cell using Potentiostat/Galvanostat PGSTAT 30. Pt disc d=1 mm was used as working electrode, Pt wire as counter electrode and Ag/AgCl as reference electrode, and 0.1M LiPF$_6$ in ethylene carbonate:diethyl carbonate EC:DEC (v/v=1/2) was used as electrolyte. The CV measurements were done at the scan rate 50 mV/s and rt. CV data are shown in FIG. 1 and FIG. 4.

Example 4

Cathode Electrode Preparation for Battery Test

The obtained materials of the present invention were eventually mixed with carbon and ethylene propylene diene monomer (EPDM) in a weight ratio 50:40:10 in cyclohexane to form a slurry. The obtained slurry was coated on aluminum foil using Doctor Blade and was dried to make the cathode electrode.

Example 5

Charging/Discharging Tests

The charging/discharging tests were performed using a Swagelock-type cell assembled under argon. The testing cells were prepared by sandwiching the separator filled with electrolyte between lithium foil 1.2 mm and the prepared composite cathode electrode (Example 3). Glass fiber (GF/D) from Whatman® was used as a separator. Lithium foil was used as counter and reference electrodes. A solution of 1 M LiN(CF$_3$SO$_2$)$_2$ in 1-ethyl-3-methylimidazolium bis(trifluoromethylsulfonyl)imide was used as electrolyte. Charge/discharge cycling was carried out between 2.8 and 4.2 V using a BaSyTec cell test system (BaSyTec GmbH). The results of charging discharging test are shown in FIGS. 2A and B, FIG. 3, FIGS. 5A and B, and FIG. 6.

The cyclic voltammogram shown in FIG. 1 recorded for 2,2',2''-(cyclopropane-1,2,3-triylidene)trimalononitrile bis lithium salt (1) demonstrates reversible redox system featuring the transfer of two electrons, as indicated by two oxidation peaks at the anodic scan and two reduction peaks during cathode scan. From the CV data, it is clear that Li$_2$C$_{12}$N$_6$ (1) shows a fully reversible redox behaviour, an important condition for applicability of this compound as active material in a rechargeable battery.

Figure 2A:
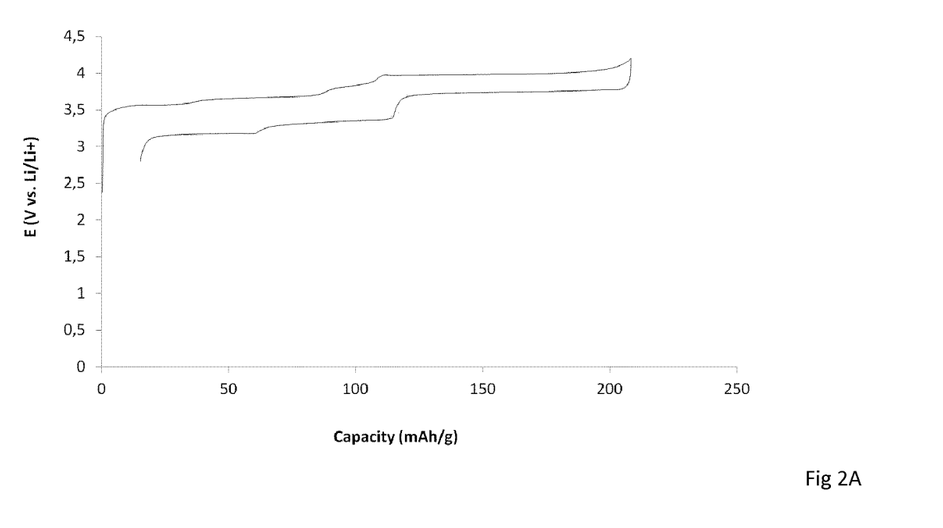
FIG. 2A shows charge/discharge at C/10 (19.3 mA/g).
Figure 2B:
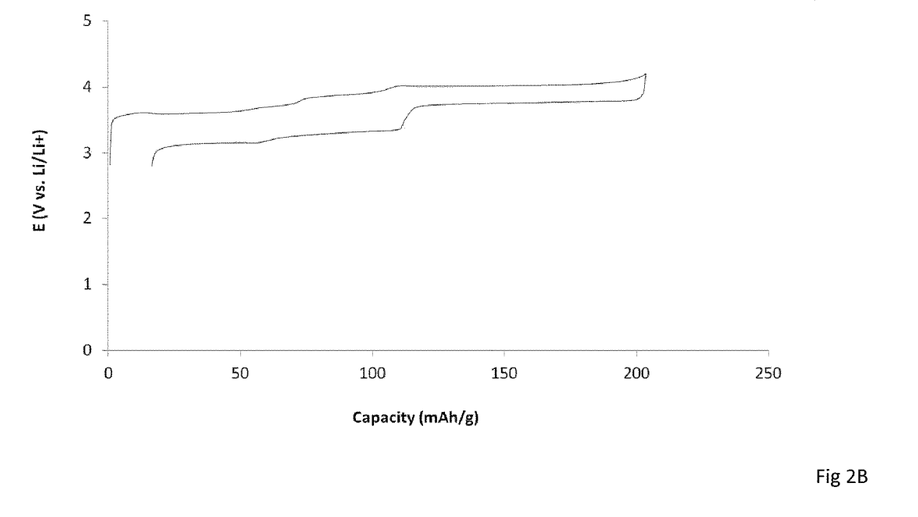
FIG. 2B shows charge/discharge at C/2 (93 mA/g).

FIGS. 2A and 2B show the first charge/discharge curves of (I) as cathode active material and lithium as anode at C/10 and C/2 rates respectively. In both curves at charging state one can see two plateaus at around 3.55 and 4 V corresponding to the oxidation of Li$_2$C$_{12}$N$_6$ under release of two lithium cations and formation of C$_{12}$N$_6$, at the discharging curve corresponding to the reduction of C$_{12}$N$_6$ to Li$_2$C$_{12}$N$_6$, two other plateaus are observed at 3.75 and 3.2 V.

The secondary battery cell using (1) as cathode material provides a high discharging capacity of 193 mAh/g at C/10 and 186 mAh/g at C/2.

It is clear from the electrochemical tests that the use of compound (1) in the cathode provides a rechargeable lithium ion battery with a higher charging and discharging voltage. The voltage of the electrochemical cell using Li$_2$C$_{12}$N$_6$ as cathode and lithium as anode after charging was 3.8V and no self discharge was observed.

Figure 3:
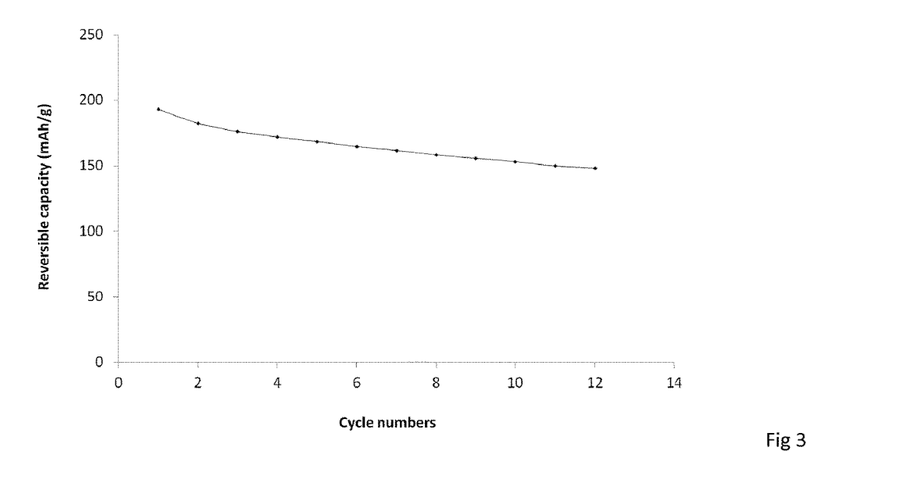
FIG. 3 shows the variation of discharge capacity with the number of cycles of 2,2',2"-(cyclopropane-1,2,3-triylidene)trimalononitrile bis lithium salt (1) as cathode, lithium metal as anode, in 1M $LiN(CF_3SO_2)$ in 1-ethyl-3-methylimidazolium bis(trifluoromethylsulfonyl)imide electrolyte

FIG. 3 illustrates the discharge capacity vs. cycle number profile of Li$_2$C$_{12}$N$_6$ (I) as cathode at C/10. Discharge capacity of 148 mAh/g remains after 12 cycles.

[4]Radialene (2) (Example 2,2'-(2,4-dioxocyclobutane-1,3-diylidene)dimalononitrile bis lithium Salt) as Cathode Material Cyclic voltammetry results presented in FIG. 4, show fully reversible behaviour.

Figure 5A:
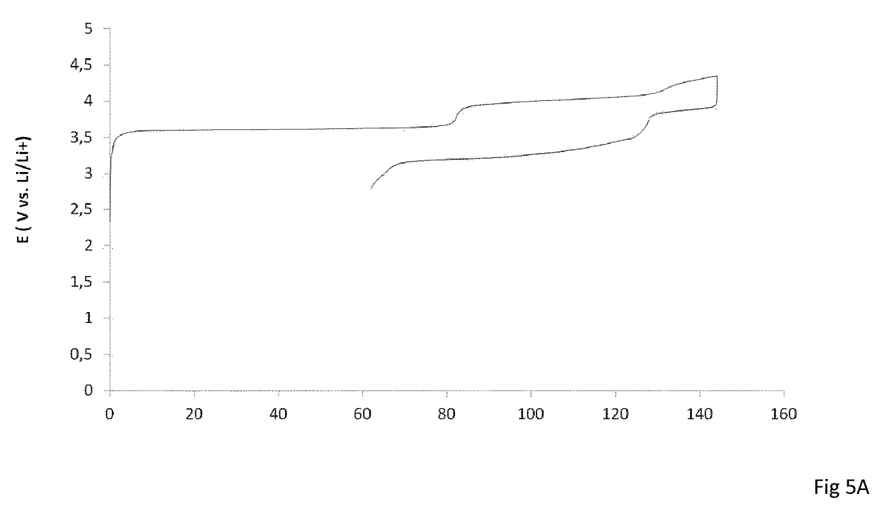
Figure 5B:
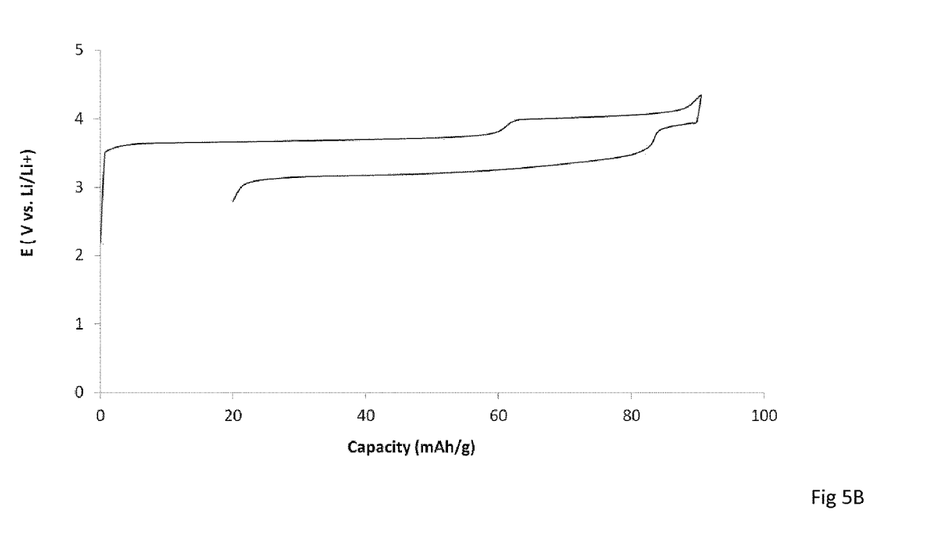

The first charge/discharge curves of the Li$_2$C$_{10}$N$_4$O$_2$ (2) as cathode active material and lithium as anode at C/10 and C/2 rates are presented in FIGS. 5A and 5B respectively. In both curves, during charging of the electrochemical cell, two plateaus are identified at around 3.6 and 4V corresponding to the oxidation of Li$_2$C$_{12}$N$_6$ (release of two lithium cations and formation of C$_{12}$N$_6$), at the discharging curve two other plateaus are observed at 3.87 and 3.2 V. The electrochemical cell using (2) as cathode material provides the discharging capacity 82 mAh/g at C/10 and 70 mAh/g at C/2.

Figure 6:
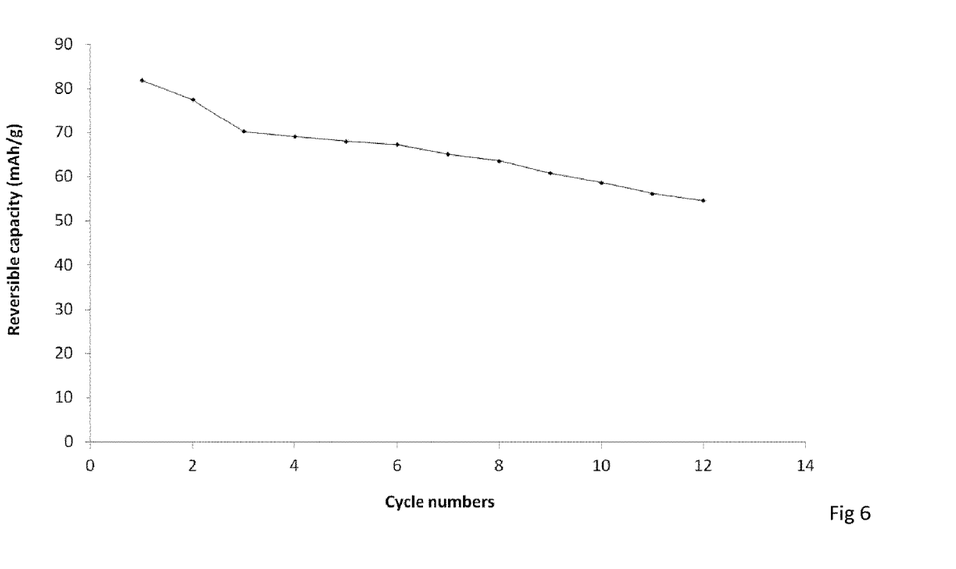
FIG. 6 shows the variation of discharge capacity with the number of cycles of 2,2'-(2,4-dioxocyclobutane-1,3-diylidene)dimalononitrile bis lithium salt (2) as cathode, lithium metal as anode, and 1M $LiN(CF_3SO_2)$ as cathode, lithium metal as anode, in 1M $LiN(CF_3SO_2)$ in 1-ethyl-3-methylimidazolium bis(trifluoromethylsulfonyl)imide electrolyte

The variation of discharge capacity with the number of cycles for the battery cell using (2) as cathode active material at C/10 is presented in FIG. 6. A 67% retention of the initial capacity was observed after 12 cycles.

The features disclosed in the foregoing description, in the claims and in the accompanying drawings may, both separately or in any combination be material for realizing the invention in diverse forms thereof.

The invention claimed is:

1. A battery comprising at least one electrochemical cell, the at least one electrochemical cell comprising a first electrode, a second electrode, a first electroactive material, a second electroactive material, and an electrolyte, wherein the electrolyte is in contact with both electrodes, and at least one of the first electroactive material or the second electroactive material comprises a radialene compound at an amount of at least 50% by weight, based on the weight of the first electroactive material or the second electroactive material, respectively, wherein the radialene compound comprises a carbocyclic core substituted with one or more groups independently selected from imino or methylidene, wherein the imino and methylidene groups are substituted with one or more electron withdrawing substituents, wherein the one or more electron withdrawing substituents are cyano groups.

2. The battery according to claim 1, wherein the first electroactive material comprises the radialene compound, and is disposed in a first compartment of the electrochemical cell, the first compartment comprising the first electrode, which is electrically connected with the positive pole of the battery.

3. The battery according to claim 1, wherein the radialene compound has the general formula (I):

wherein $Z^1$, $Z^2$ and $Z^3$ are independently selected from dicyanomethylidene, or a cyanimino group, x is an integer selected from 1 or 2, y is an integer selected from 0, 1 or 2, and the dashed lines represent the following when y is 0, 1, or 2—
i) when y is 0,
6 electrons delocalized over 6 bonds if x is 1, and
8 electrons delocalized over 8 bonds if x is 2,
ii) when y is 1,
7 electrons delocalized over 6 bonds if x is 1, and
9 electrons delocalized over 8 bonds if x is 2, and
iii) when y is 2,
8 electrons delocalized over 6 bonds if x is 1, and
10 electrons delocalized over 8 bonds if x is 2.

4. The battery according to claim 3, wherein at least one of $Z^1$ and $Z^2$, and at least one $Z^3$ is dicyanomethylidene.

5. The battery according to claim 1, wherein the electrolyte comprises alkali metal cations.

6. The battery according to claim 1, wherein the first electroactive material in its reduced state comprises alkali metal cations.

7. The battery according to claim 1, wherein the second electroactive material in its reduced state comprises an alkali metal.

8. The battery according to claim 6, wherein the alkali metal cations are lithium cations.

9. The battery according to claim 7, wherein the alkali metal is Li.

10. An electroactive material comprising a radialene compound, wherein the electroactive material is solid or gel-like.

11. A compound having formula (II):

wherein $Z^1$, $Z^2$, and $Z^3$ are independently selected from dicyanomethylidene or a cyanimino group, x is an integer selected from 1 or 2, the dashed lines represent 8 electrons delocalized over 6 bonds if x is 1, and 10 electrons delocalized over 8 bonds if x is 2, and excluding a compound of formula (II) wherein [i] x is 1, and [ii] $Z^1$, $Z^2$, and $Z^3$ are dicyanomethylidene.

12. The compound according to claim 11, wherein at least one of $Z^1$ and $Z^2$, and at least one $Z^3$ is dicyanomethylidene.

* * * * *